United States Patent [19]
Rich et al.

[11] Patent Number: 5,230,093
[45] Date of Patent: Jul. 20, 1993

[54] TRANSMITTER FILTER WITH INTEGRAL DIRECTIONAL COUPLER FOR CELLULAR TELEPHONES

[76] Inventors: Randall W. Rich, 1543 Winslowe Dr., Palatine, Ill. 60067; Dale G. Schwent, 1425 Jefferson Rd., Hoffman Estates, Ill. 60195; Rashid M. Osmani, 621 Hiawatha Dr., Carol Stream, Ill. 60188

[21] Appl. No.: 695,500

[22] Filed: May 3, 1991

[51] Int. Cl.$^5$ .................. H04B 1/04; H01P 1/20
[52] U.S. Cl. .................. 455/126; 455/83; 455/116; 333/202
[58] Field of Search .................. 455/82–83, 455/116, 127, 337–340, 126; 379/58–59; 333/202, 202 DB

[56] References Cited
U.S. PATENT DOCUMENTS

| | | | |
|---|---|---|---|
| 4,431,977 | 2/1984 | Sokola et al. | 333/202 |
| 4,768,003 | 8/1988 | Kawakami et al. | 333/202 |
| 4,870,698 | 9/1989 | Katsuyama et al. | 455/127 |
| 4,879,533 | 11/1989 | de Muro et al. | 333/202 |
| 5,010,309 | 4/1991 | Manssen et al. | 455/82 |
| 5,020,093 | 5/1991 | Pireh | 379/59 |
| 5,045,824 | 9/1991 | Metroka | 333/202 |
| 5,109,536 | 4/1992 | Kommrusch | 333/202 |

*Primary Examiner*—Reinhard J. Eisenzopf
*Assistant Examiner*—Andrew Faile

[57] ABSTRACT

A cellular telephone transmitter (100) includes a variable-gain power amplifier (102), the output of which is filtered and sampled by a filter (104) with an integral directional coupler. Filter (104) includes both a transmitter signal filter and a directional coupler on a ceramic block of one or more pieces. The directional coupler has been realized by two coupled transmission lines provided by the two holes (206 and 207) on the left side of the ceramic block, and the transmitter filter has been realized by five short-circuited coupled transmission lines provided by the five holes (201–205) on the right side of the ceramic block.

56 Claims, 3 Drawing Sheets

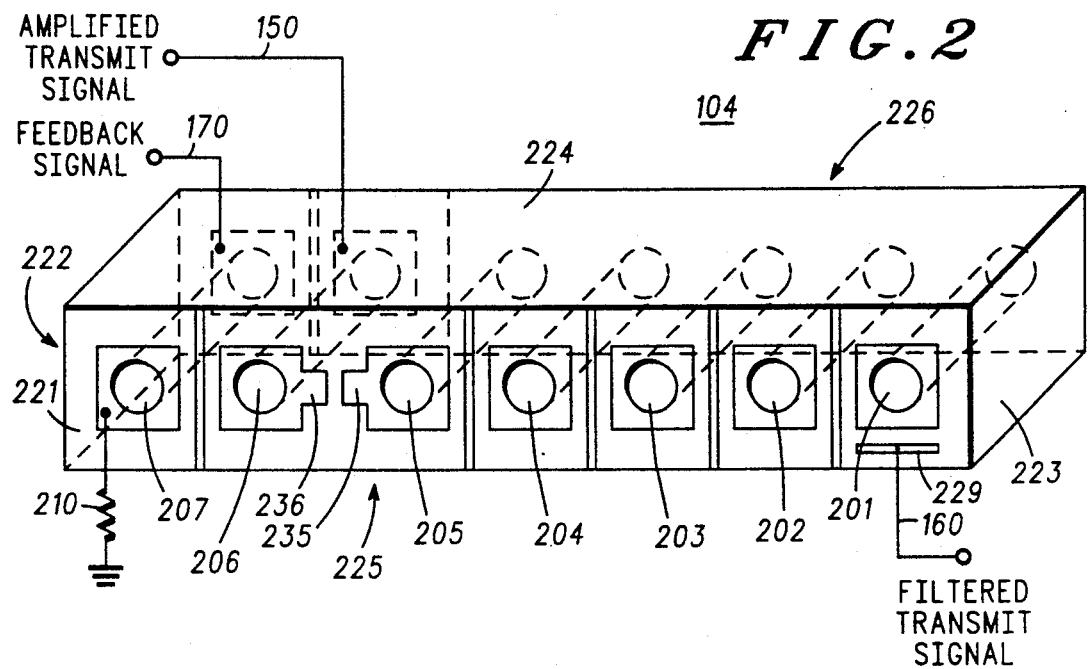

TRANSMITTER FILTER WITH INTEGRAL DIRECTIONAL COUPLER FOR CELLULAR TELEPHONES

BACKGROUND OF THE INVENTION

The present invention is generally related to radio frequency filters, and more particularly to a transmitter filter with an integral directional coupler for use in radio signal transmitters such as cellular telephones.

In cellular telephones, it is necessary to accurately maintain the magnitude of the output power at one of eight different levels during cellular telephone calls. Such cellular telephones typically include power control circuitry of the type described in U.S. Pat. No. 4,523,155 for accurately maintaining the magnitude of the output power at the desired power level. The magnitude of the output power from the cellular telephone transmitter may be sampled by a capacitor, as illustrated in U.S. Pat. No. 4,523,155, or by a directional coupler. A directional coupler is preferable over a capacitor since it only detects power in the forward direction. Such directional couplers are typically implemented on printed circuit boards by means of adjacent, parallel coupled transmission lines, one line coupling the power amplifier to the transmitter filter and the second lien terminated on one end and coupled to detecting circuitry on the other end for producing an output signal having a magnitude proportional to the magnitude of the power amplifier output signal. However, directional couplers implemented on certain printed circuit boards are inadequate since their net insertion loss is no better than approximately 0.7 dB, their unloaded q is no better than approximately 40, and their characteristic impedance can vary by approximately 10% due to dimensional tolerances. For the foregoing reasons, there is a need for an improved transmitter filter with integral directional coupler for use in radio signal transmitters such as cellular telephones.

SUMMARY OF THE INVENTION

The present invention encompasses a filter for coupling a radio frequency (RF) signal from a signal source to an antenna and producing a feedback signal having a magnitude proportional to the magnitude of the RF signal. The filter comprises: a dielectric block of one or more pieces having top, bottom and side surfaces and having at least first, second, and third holes each having a first end on the top surface, having a second end on the bottom surface, and being aligned with one another, the second hole spaced apart from the third hole by a predetermined distance for controlling coupling therebetween, the side surfaces and the first, second, and third holes being substantially covered with a conductive material, and the portion of the bottom surface near the second end of the third hole also being substantially covered with a conductive material; a first coupler for coupling the second end of the second hole to the transmitter; a second coupler for coupling the first end of the third hole to the antenna; a third coupler coupled to the second end of the first hole for providing the feedback signal; and an impedance coupled to the first end of the first hole.

BRIEF DESCRIPTION OF THE DRAWINGS

FIG. 2 is a perspective view of transmitter filter with integral directional coupler 104 in FIG. 1, embodying the present invention;

FIG. 3 is an equivalent circuit diagram for transmitter filter with integral directional coupler 104 in FIG. 2.

FIG. 4 is a bottom view of transmitter filter with integral directional coupler 104 in FIG. 2.

DESCRIPTION OF THE PREFERRED EMBODIMENT

Figure 1:
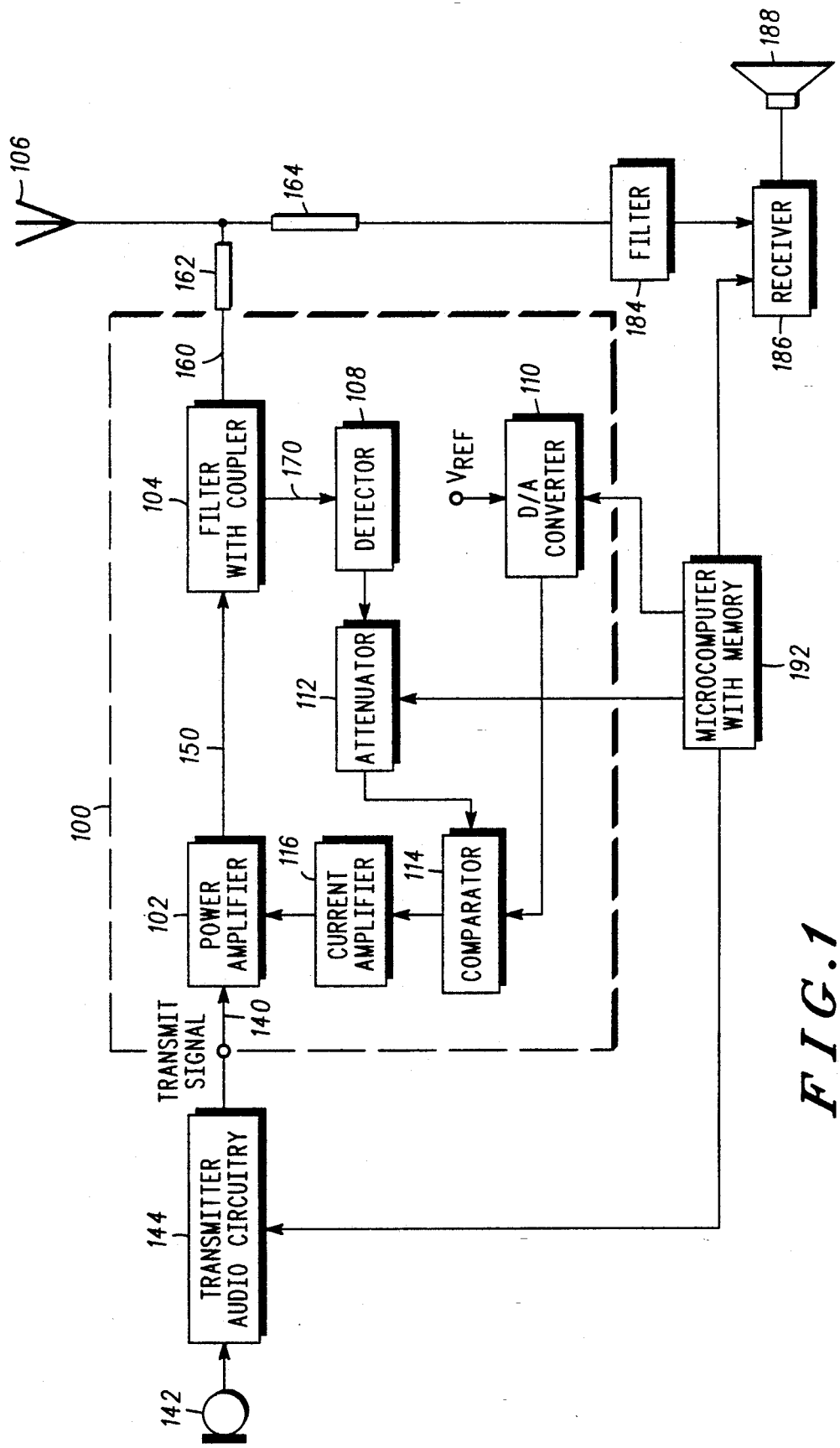
FIG. 1 is a block diagram of a cellular telephone including transmitter circuitry 100, which may advantageously utilize the present invention.

Referring to FIG. 1, there is illustrated a block diagram of a cellular telephone including microcomputer 192 with memory therein for controlling the operation thereof, antenna 106 receiver 186 coupled by transmission line 164 and filter 184 to antenna 106, and transmitter circuitry 100 coupled by transmission line 162 to antenna 106 and including transmitter filter with integral directional coupler 104 embodying the present invention. Transmitter filter with integral directional coupler 104 may be used in any conventional cellular telephone, such as, for example, the transceiver shown and described in Motorola instruction manual number 68P81066E40, entitled "DYNATAC Cellular Mobile Telephone 800 MHZ Transceiver," or the portable transceiver shown and described in Motorola instruction manual number 68P81054E60, entitled "DYNA-TAC Cellular Portable Telephone G-Series," both published by and available from Motorola C & E Parts, 1313 East Algonquin Road, Schaumburg, Ill. 60196, U.S.A.

Transmitter circuitry 100 is responsive to a level control signal from microcomputer 192 for maintaining the output power of transmitter signal 150 at a selected one of eight different power levels. In the preferred embodiment, the power levels range from ten milliwatts to six watts. Data including a selected power level is sent by a cellular base station, received by receiver 186, and decoded by microcomputer 192 in order to determine which of the eight different power levels at which transmitter circuitry 100 is to operate. Microcomputer 192 codes the level control signal as a digital word having a magnitude corresponding to the determined power level. The level control signal has one of eight different magnitudes corresponding to the eight different power levels, respectively.

Transmitter circuitry 100 includes power amplifier 102 which has a variable gain for amplifying transmit signal 140 to produce transmitter signal 150, that is coupled by filter 104 and transmission line 162 to antenna 106. Power amplifier 102 is responsive to a amplified drive signal from current/voltage amplifier 116 for varying the output power of transmitter signal 150. Detector 108 is coupled to the feedback signal 170 from filter 104 for producing an output power signal. Attenuator 112 is coupled to a control signal from microcomputer 192 for attenuating the output power signal from detector 108 by a predetermined amount for the top four of eight different power levels. The attenuated output power signal from attenuator 112 is applied to comparator 114. Digital-analog (D/A) converter 110 is coupled to reference voltage Vref and the level control signal from microcomputer 192 for converting the level control signal to ne of eight different reference voltages corresponding to the eight different power levels, respectively. Comparator 114 compares the attenuated output power signal from attenuator 112 to the voltage from D/A converter 110 to produce a drive signal, which is amplified by current/voltage amplifier 116. As the amplified drive signal is increased, the power of the transmitter signal 150 is increased, and vice versa.

Referring next to FIG. 2, there is illustrated a perspective view of transmitter filter with integral directional coupler 104 in FIG. 1. According to a feature of present invention, filter 104 includes both a transmitter signal filter and a directional coupler on one ceramic block. The directional coupler has been realized by two coupled transmission lines provided by holes 206 and 207 on the left side of ceramic block 104. In other embodiments, the directional coupler may be provided by two holes on the right side of ceramic block 104, or by two holes in the middle of ceramic block 104 between two filters provided by other holes. The transmitter filter has been realized by five short-circuited coupled transmission lines provided by holes 201-205 on the right side of ceramic block 104.

The directional coupler of filter 104 is substantially improved over prior art printed-circuit board directional couplers in both electrical performance and physical characteristics. The unloaded Q of the transmission lines 206 and 207 may be greater then 400 using commercially available ceramic materials in block 104. The net insertion loss is approximately 0.2 dB for 17 dB coupling. The efficiency of power amplifier 102 is much better, since the dimensions of the hole diameter and width of block 104 vary by less than 2%. Space requirements are also minimized since the physical length of transmission liens 206 and 027 is reduced due to the high dielectric constant of the ceramic material in block 104. In addition, the impedance of the directional coupler of filter 104 is much less than fifty ohms, which is desired for optimal matching to the output of power amplifier 102.

Block 104 may be comprised of any suitable commercially available dielectric material that has low loss, a high dielectric constant, and a low temperature coefficient of dielectric constant. A suitable ceramic material for block 104 is the ceramic compound including a barium oxide, titanium oxide, and zirconium oxide, the electrical characteristics of which are described in more detail in an article by G. H. Jonker and W. Kwestroo, entitled "The Ternary Systems $BaO-TiO_2-SnO_2$ and $BaO-TiO_2-ZrO_2$", published in the Journal of the American Ceramic Society, volume 41, number 10, at pages 390-394, October 1958. Of the ceramic compounds described in this article, the compound in Table VI having the composition 18.5 mole percent BaO, 77.0 mole percent $TiO_2$, and 4.5 mole percent $ZrO_2$, and having a dielectric constant of 40 is well suited for use in ceramic block 104.

Holes 201-207 have surfaces covered at least in part by conductive material for producing transmission lines. On top surface 221 of ceramic block 104, each hole 201-207 is coupled to a corresponding electrode comprised of conductive material and disposed thereon. Bottom surface 26 of ceramic block 104 is covered by conductive material except for the area surrounding holes 206 and 207. On bottom surface 226, each of holes 206 and 207 are also coupled to a corresponding electrode comprised of conductive material. The electrodes of holes 201-207 on the top and bottom surfaces 221 and 226 have a substantially square shape, although they may be shaped as a rectangle, parallelogram, ellipse, circle, or any other suitable configuration. The electrodes of holes 201-205 on top surface 221 and the electrodes of holes 206 and 207 on top surface 221 and bottom surface 226 are also separated from each other by a thin portion of grounded conductive material extending from side 224 to side 225. In other embodiments, these thin portions of grounded conductive material may have a gap in them or may be deleted. The electrode of hole 201 is also capacitively coupled to output electrode 229 for providing filtered transmit signal 160. In other embodiments, filtered transmit signal 160 may be provided by a wire connected to the electrode of hole 201, by a coupling electrode which inserts into hole 201, or by any other suitable means.

Holes 201-205 have short-circuit end on bottom surface 226 and an open-circuit end on top surface 221. Each electrode of holes 201-205 is capacitively coupled to the surrounding conductive material of the separating strips, sides 224 and 225, and/or ends 222 and 223 for essentially producing a foreshortened transmission line or resonator. The electrical length of holes 201-205 may be varied by removing conductive material near the open-circuit end from the electrodes thereof or from the surrounding conductive material as well as from the conductive material near the short-circuit end. The electrical characteristics of the transmission lines provided by holes 201-207 may b varied by any suitable conventional techniques, such as, for example, those illustrated and described in U.S. Pat. No. 4,800,348.

Referring next to FIG. 4, there is illustrated a bottom view of transmitter filter 104 in FIG. 2. Bottom surface 226 is covered with conductive material except for portions surrounding holes 206 and 207. The conductive material on bottom surface 226 is coupled to electrical signal ground. As described hereinabove, holes 206 and 207 are coupled to corresponding electrodes comprised of conductive material and disposed on bottom surface 226. The electrodes of holes 206 and 207 may also be separated from each other by a thin potion of grounded conductive material extending from side 224 to side 225. Signals may be connected to the transmission lines provided by holes 206 and 207 by connecting wires thereto, by electrodes 226 and 227, respectively, by coupling electrodes which insert into holes 206 and 207, or by any other suitable means.

Referring next to FIG. 3, there is illustrated an equivalent circuit diagram for transmitter filter with integral directional coupler 104 in FIG. 2. Holes 201-205 are illustrated as short-circuited transmission lines 201-205, respectively, each having a top-surface end coupled by a capacitor to electrical signal ground and a bottom-surface end coupled to electrical signal ground. Holes 206 and 207 are illustrated as transmission lines 206 and 207, respectively, each having a top-surface end coupled by a capacitor to electrical signal ground and a bottom-surface end coupled by a capacitor to electrical signal ground. Filtered transmit signal 160 is provided at output electrode 229, which is coupled by a capacitor to the top-surface end of transmission line 201 and by another capacitor to electrical signal ground. Amplified transmit signal 150 from power amplifier 102 is coupled to the bottom-surface end of transmission line 206. Feedback signal 170 is provided at the bottom-surface end of transmission line 207. The top-surface end of transmission line 207 is coupled to impedance 210, which is in the preferred embodiment, is 13.5 ohms.

Transmission lines 206 and 207 are close enough to one another to be intercoupled through the ceramic material of block 104. The intercoupling between holes 206 and 207 may be controlled by varying the distance between the holes to achieve the desired amount of intercoupling through the ceramic material of block 104. Capacitive intercoupling between the top-surface ends and between the bottom-surface ends of transmission lines 206 and 207 is reduced by the grounded conductive material separating them.

The electrodes of holes 206 and 205 have portions 236 and 235, respectively, that extend toward and oppose one another for capacitively intercoupling transmission lines 206 and 205, where the amount of capacitive intercoupling is determined by the distance between the opposing portions 236 and 235. Transmission lines 206 and 205 are sufficiently separated from one another to reduce intercoupling through the ceramic material of block 104. In other embodiment, intercoupling through the ceramic material of block 104 may also be reduced by slots (covered with conductive material) in side surfaces 224 and 225 between holes 206 and 205, by an additional hole (not covered with conductive material) extending from top surface 221 to bottom surface 226 between holes 206 and 205, or by conductive material interposed therebetween as shown in FIG. 5.

Transmission lies 201-205 are close enough to one another to be intercoupled through the ceramic material of block 104. The intercoupling between holes 201-205 may be controlled by varying the distance between the holes to achieve the desired amount of intercoupling through the ceramic material of block 104. Capacitive intercoupling between the top-surface ends ends of transmission lines 201-205 is reduced by the grounded conductive material separating them. In other embodiments, pairs of electrodes of holes 201-205 may have portions similar to portions 236 and 235, that extend toward and oppose one another for capacitively intercoupling selected pairs of transmission lines 201-205.

Figure 5:
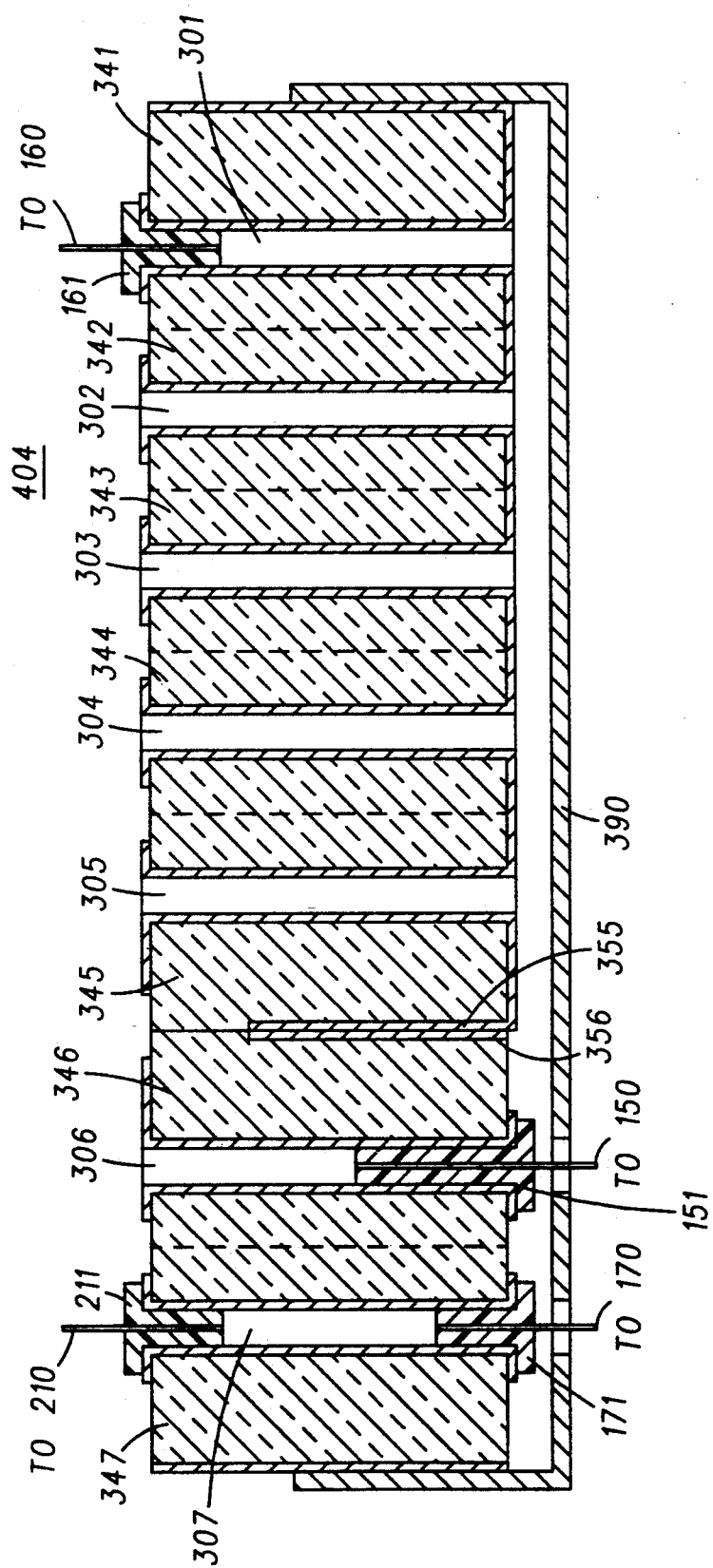
FIG. 5 is a cross sectional view of an alternative embodiment of a transmitter filter with integral directional coupler 404, embodying the present invention.

Referring next to FIG. 5, there is illustrated a cross sectional view of an alternative embodiment of a transmitter filter with integral directional coupler 404, embodying the present invention. Filter 404 includes a directional coupler realized by two coupled transmission lines provided by holes 306 and 307 in separate ceramic blocks 346-347, and a transmitter signal filter realized by five short-circuited coupled transmission lines provided by holes 301-305 in separate ceramic block 341-345. In other embodiments, separate blocks 341-347 may be provided for each hole 301-307, respectively, as illustrated by the dashed lines between the holes.

Ceramic blocks 346-347 and 341-345 inclued conductive material 356 and 355 on adjoining end surfaces for reducing the amount of intercoupling through the ceramic material between holes 306 and 305, respectively. The intercoupling through the ceramic material between holes 306 and 305 may be further reduced by increasing the size of conductive material 356 and 355. In other embodiments, conductive material 356 and 355 nee only be on one of the end surfaces of either block 346-347 or block 341-345.

Ceramic blocks 346-347 and 341-345 are attached to ne another and retained by housing 390 which encloses the bottom surface and extends partially over the end surfaces and side surfaces of block 404. Housing 390 may be soldered to the conductive material on the end surfaces and side surfaces of block 404. In other embodiments not including housing 390, ceramic blocks 346-347 and 341-345 may be attached to one another by solder, adhesive, or other suitable bonding means. Filter 404 includes electrodes with insulating couplers 151, 161, 171, and 211 for coupling amplified transmit signal 150, filtered transmit signal 160, feedback signal 170 and impedance 210 to corresponding holes 306, 301, 307 and 307, respectively. Electrodes with insulating couplers 151 and 171 project through holes in housing 390 and are retained in holes 306 and 307, respectively, by housing 390. Electrodes with insulating couplers 161 and 211 may be retained in holes 301 and 307, respectively, by means of a press fit, adhesives or a top housing similar to housing 390.

In summary, a unique filter 104 and 404 includes both a transmitter signal filter and a directional coupler on one or more ceramic blocks. In filter 104, the directional coupler has been realized by two coupled transmission lines provided by holes 206 and 207 on the left side of ceramic block 104, and the transmitter filter has been realized by five short-circuited coupled transmission lines provided by holes 201-205 on the right side of ceramic block 104. In other embodiments a filter 104, the directional coupler may be realized by two holes on the right side of ceramic block 104, or by two holes in the middle of ceramic block 104 between two filters provided by other holes. In filter 404, the directional coupler is provided by separate ceramic block 346-347, and is attached to the transmitter filter provided by separate ceramic block 341-345. The novel filter of the present invention may be advantageously utilized in transmitter circuitry of cellular telephones and other radios where it is necessary to sample and control the magnitude of the transmitter signal.

We claim:

1. A filter for coupling a radio frequency (RF) signal from a signal source to an antenna and producing a feedback signal having a magnitude proportional to the magnitude of the RF signal, said filter comprising:

a dielectric block having top, bottom and side surfaces and having at least first, second, and third holes each having a first end on the top surface having a second end on the bottom surface, and being aligned with one another, said first hole spaced apart from said second hole by a predetermined distance for controlling coupling therebetween, said side surfaces and said first, second, and third holes being substantially covered with a conductive material, and the portion of said bottom surface near the second end of said third hole also being substantially covered with a conductive material;

first coupling means coupling the second end of said second hole to the RF signal;

second coupling means coupling the first end of said third hole to the antenna;

third coupling means coupled to the second end of said first hole for providing the feedback signal; and impedance means coupled to the first end of said first hole.

2. The filter of claim 1, wherein said dielectric block further includes first and second conductive material portions disposed on the top and bottom surfaces, respectively, between said first and second holes and being connected to the conductive material covering the sides.

3. The filter of claim 1, further including first, second and third electrode means comprised of a conductive material, disposed on the top surface, and coupled to the first end of said first, second and third holes, respectively.

4. The filter of claim 3, wherein said first, second and third electrode means each have the shape of a parallelogram.

5. The filter of claim 3, further including fourth and fifth electrode means comprised of a conductive material, disposed on the bottom surface, and coupled to the second end of said first and second holes, respectively.

6. The filter of claim 5, wherein said fourth and fifth electrode means each have the shape of a parallelogram.

7. The filter of claim 3, wherein said second and third electrode means include respective portions extending toward and opposing one another for capacitively intercoupling said second and third holes, respectively.

8. The filter of claim 1, wherein said second coupling means includes electrode means comprised of a conductive material and disposed on the top surface at a predetermined distance from the third hole.

9. The filter of claim 1, wherein said first coupling means includes electrode means comprised of a conductive material and disposed on the bottom surface at a predetermined distance from the second hole.

10. The filter of claim 1, wherein said third coupling means includes electrode means comprised of a conductive material and disposed on the bottom surface at a predetermined distance from the first hole.

11. A radio, comprising:
an antenna;
a transmitter having variable gain for producing a transmitter signal;
control means responsive to a feedback signal for controlling the variable gain of the transmitter; and
a filter for coupling the transmitter signal to the antenna, comprising:
a dielectric block having top, bottom and side surfaces and having at first, second, and third holes each having a first end on the top surface, having a second end on the bottom surface, and being aligned with one another, said first hole spaced apart from said second hole by a predetermined distance for controlling coupling therebetween, said side surfaces and said first, second, and third holes being substantially covered with a conductive material, and the portion of said bottom surface near the second end of said third hole also being substantially covered with a conductive material;
first coupling means coupling the second end of said second hole to the transmitter signal;
second coupling means coupling the first end of said third hole to the antenna;
third coupling means coupled to the second end of said first hole for providing the feedback signal; and
impedance means coupled to the first end of said first hole.

12. The radio of claim 11, wherein said dielectric block further includes first and second conductive material portions disposed on the top and bottom surfaces, respectively, between said first and second holes and being connected to the conductive material covering the sides.

13. The radio of claim 11, further including first, second and third electrode means comprised of a conductive material, disposed on the top surface, and coupled to the first end of said first, second and third holes, respectively.

14. The radio of claim 13, wherein said first, second and third electrode means each have the shape of a parallelogram.

15. The radio of claim 13, further including fourth and fifth electrode means comprised of a conductive material, disposed on the bottom surface, and coupled to the second end of said first and second holes, respectively.

16. The radio of claim 15, wherein said fourth and fifth electrode means each have the shape of a parallelogram.

17. The radio of claim 13, wherein said second and third electrode means include respective portions extending toward and opposing one another for capacitively intercoupling said second and third holes, respectively.

18. The radio of claim 11, wherein said second coupling means includes electrode means comprised of a conductive material and disposed on the top surface at a predetermined distance from the third hole.

19. The radio of claim 11, wherein said first coupling means includes electrode means comprised of a conductive material and disposed on the bottom surface at a predetermined distance from the second hole.

20. The radio of claim 11, wherein said third coupling means includes electrode means comprised of a conductive material and disposed on the bottom surface at a predetermined distance from the first hole.

21. A filter for coupling a radio frequency (RF) signal from a signal source to an antenna and providing a feedback signal having a magnitude proportional to the magnitude of the RF signal, said filter comprising:
a first dielectric block having top, bottom, first and second end, and first and second side surfaces and having at least first and second holes each having a first end on the top surface, having a second end on the bottom surface, and being aligned with one another between said first and second ends, respectively, said first hole spaced apart from said second hole by a predetermined distance for controlling coupling therebetween, and said first end surface, said first and second side surfaces, and said first and second holes being substantially covered with a conductive material;
a second dielectric block having top, bottom, first and second end, and first and second side surfaces and having at least first and second holes each having a first end on the top surface, having a second end on the bottom surface, and being aligned with one another, said first hole spaced apart from said second hole by a predetermined distance for controlling coupling therebetween, and said second end surface, said first and second side surfaces, said bottom surface, and said first and second holes being substantially covered with a conductive material;
means for attaching the second end surface of said first dielectric block to said first end surface of said second dielectric block;
impedance means coupled to the first end of said first hole in said first dielectric block;

first coupling means coupling the RF signal to the second end of said second hole in said first dielectric block;

second coupling means coupled to the second end of said first hole in said first dielectric block for providing the feedback signal; and third coupling means coupling the antenna to the first end of said second hole in said second dielectric block.

22. The filter of claim 21, wherein said first dielectric block further includes first and second conductive material portions disposed on the top and bottom surfaces, respectively, between said first and second holes and being connected to the conductive material covering the first and second sides.

23. The filter of claim 21, wherein said second dielectric block further includes first and second conductive material portions disposed on the top surface between said first and second holes and being connected to the conductive material covering the first and second sides.

24. The filter of claim 21, wherein said first dielectric block further includes first and second electrode means comprised of a conductive material, disposed on the top surface, and coupled to the first end of said first and second holes, respectively.

25. The filter of claim 24, wherein said first and second electrode means each have the shape of a parallelogram.

26. The filter of claim 24, wherein said first dielectric block further includes third and fourth electrode means comprised of a conductive material, disposed on the bottom surface, and coupled to the second end of said first and second holes, respectively.

27. The filter of claim 26, wherein said third and fourth electrode means each have the shape of a parallelogram.

28. The filter of claim 21, wherein said second dielectric block further includes first and second electrode means comprised of a conductive material, disposed on the top surface, and coupled to the first end of said first and second holes, respectively.

29. The filter of claim 28, wherein said first and second electrode means each have the shape of a parallelogram.

30. The filter of claim 21, wherein said first dielectric block further includes first electrode means comprises of a conductive material, disposed on the top surface, and coupled to the first end of said second hole, wherein said second dielectric block further includes second electrode means comprised of a conductive material, disposed on the top surface, and coupled to the first end of said first hole, and wherein said first and second electrode means include respective portions extending toward and opposing one another for capacitively intercoupling said second hole in said first dielectric block and said first hole in said second dielectric block.

31. The filter of claim 30, wherein said first and second electrode means each have the shape of a parallelogram.

32. The filter of claim 21, wherein said first coupling means includes electrode means comprised of a conductive material and disposed on the top surface at a predetermined distance from the first hole in said first dielectric block.

33. The filter of claim 21, wherein said second coupling means includes electrode means comprised of a conductive material and disposed on the top surface at a predetermined distance from the second hole in said first dielectric block.

34. The filter of claim 21, wherein said third coupling means includes electrode means comprised of a conductive material and disposed on the top surface at a predetermined distance from the second hole in said second dielectric block.

35. The filter of claim 21, wherein said second end surface of said first dielectric block is covered at least partially by conductive material for controlling the coupling between said second hole in said first dielectric block and said first hole in said second dielectric block.

36. The filter of claim 21, wherein said first end surface of said second dielectric block is covered at least partially by conductive material for controlling the coupling between said second hole in said first dielectric block and said first hole in said second dielectric block.

37. The filter of claim 21, wherein said means for attaching further includes bracket means for at least partially enclosing said first and second dielectric blocks.

38. A radio, comprising:

an antenna;

a transmitter having variable gain for producing a transmitter signal;

control means responsive to a feedback signal for controlling the variable gain of a transmitter; and a filter for coupling the transmitter signal to the antenna, comprising:

a first dielectric block having top, bottom first and second end, and first and second side surfaces and having at least first and second holes each having a first end on the top surface, having a second end on the bottom surface, and being aligned with one another between said first and second ends, respectively, said first hole spaced apart from said second hole by a predetermined distance for controlling coupling therebetween, and said first end surface, said first and second side surfaces, and said first and second holes being substantially covered with a conductive material;

a second dielectric block having top, bottom, first and second end, and first and second side surfaces and having at least first and second holes each having a first end on the top surface, having a second end on the bottom surface, and being aligned with one another, said first hole spaced apart from said second hole by a predetermined distance for controlling coupling therebetween, and said second end surface, said first and second side surfaces, said bottom surface, and said first and second holes being substantially covered with a conductive material;

means for attaching the second end surface of said first dielectric block to said first end surface of said second dielectric block;

impedance means coupled to the first end of said first hole in said first dielectric block;

first coupling means coupling the transmitter signal to the second end of said second hole in said first dielectric block;

second coupling means coupled to the second end of said first hole in said first dielectric block for providing the feedback signal; and third coupling means coupling the antenna to the first end of said second hole in said second dielectric block.

39. The radio of claim 38, wherein said first dielectric block further includes first and second conductive material portions disposed on the top and bottom surfaces, respectively, between said first and second holes and being connected to the conductive material covering the first and second sides.

40. The radio of claim 38, wherein said second dielectric block further includes first and second conductive material portions disposed on the top surface between said first and second holes and being connected to the conductive material covering the first and second sides.

41. The radio of claim 38, wherein said first dielectric block further includes first and second electrode means comprised of a conductive material, disposed on the top surface, and coupled to the first end of said first and second holes, respectively.

42. The radio of claim 41, wherein said first and second electrode means each have the shape of a parallelogram.

43. The radio of claim 41, wherein said first dielectric block further includes third and fourth electrode means comprised of a conductive material, disposed on the bottom surface, and coupled to the second end of said first and second holes, respectively.

44. The radio of claim 43, wherein said third and fourth electrode means each have the shape of a parallelogram.

45. The radio of claim 38, wherein said second dielectric block further includes first and second electrode means comprised of a conductive material, disposed on the top surface, and coupled to the first end of said first and second holes, respectively.

46. The radio of claim 45, wherein said first and second electrode means each have the shape of a parallelogram.

47. The radio of claim 38, wherein said first dielectric block further includes first electrode means comprised of a conductive material, disposed on the top surface, and coupled to the first end of said second hole, wherein said second dielectric block further includes second electrode means comprised of a conductive material, disposed on the top surface, and coupled to the first end of said first hole, and wherein said first and second electrode means include respective portions extending toward and opposing one another for capacitively intercoupling said second hole in said first dielectric block and said first hole in said second dielectric block.

48. The radio of claim 47, wherein said first and second electrode means each have the shape of a parallelogram.

49. The radio of claim 38, wherein said first coupling means includes electrode means comprised of a conductive material and disposed on the top surface at a predetermined distance from the first hole in said first dielectric block.

50. The radio of claim 38, wherein said second coupling means includes electrode means comprised of a conductive material and disposed on the top surface at a predetermined distance from the second hole in said first dielectric block.

51. The radio of claim 38, wherein said third coupling means includes electrode means comprised of a conductive material and disposed on the top surface at a predetermined distance from the second hole in said second dielectric block.

52. The radio of claim 38, wherein said second side surface of said first dielectric block is covered at least partially by conductive material for controlling the coupling between said second hole in said first dielectric block and said first hole in said second dielectric block.

53. The radio of claim 38, wherein said first side surface of said second dielectric block is covered at least partially by conductive material for controlling the coupling between said second hole in said first dielectric block and said first hole in said second dielectric block.

54. The radio of claim 38, wherein said means for attaching further includes bracket means for at least partially enclosing said first and second dielectric blocks.

55. A filter for coupling a radio frequency (RF) signal from a signal source to an antenna and producing a feedback signal having a magnitude proportional to the magnitude of the RF signal, said filter comprising:
a first dielectric block having top, bottom, first and second end, and first and second side surfaces and having at least a first hole having a first end on the top surface, having a second end on the bottom surface, and being disposed between said first and second ends, respectively, and said first end surface, said first and second side surfaces, and said first hole being substantially covered with a conductive material;
a second dielectric block having top, bottom, first and second end, and first and second side surfaces and having at least a second hole having a first end on the top surface, having a second end on the bottom surface, being aligned with the first hole, and being disposed between said first and second ends, said first hole spaced apart from said second hole by a predetermined distance for controlling coupling therebetween, and said first and second side surface, and said second hole being substantially covered with a conductive material;
a third dielectric block having top, bottom, first and second end, and first and second side surfaces and having at least a third hole having a first end on the top surface, having a second end on the bottom surface, being aligned with the second hole, and being disposed between said first and second ends, and said second end surface, said first and second side surfaces, said bottom surface, and third hole being substantially covered with a conductive material;
means for attaching the second end surface of said first dielectric block to said first end surface of said second dielectric block and attaching the second end surface of said second dielectric block to said first end surface of said third dielectric block;
impedance means coupled to the first end of said first hole in said first dielectric block;
first coupling means coupling the RF signal to the second end of said second hole in said dielectric block;
second coupling means coupled to the second end of said first hole in said first dielectric block for providing the feedback signal; and
third coupling means coupling the antenna to the first end of said third hole in said third dielectric block.

56. A radio, comprising:
an antenna;
a transmitter having variable gain for producing a transmitter signal;
control means responsive to a feedback signal for controlling the variable gain of the transmitter; and
a filter for coupling the transmitter signal to the antenna, comprising:

a first dielectric block having top, bottom, first and second end, and first and second side surfaces and having at least a first hole having a first end on the top surface, having a second end on the bottom surface, and being disposed between said first and second ends, respectively, and said first end surface, said first and second side surfaces, and said first hole being substantially covered with a conductive material;

a second dielectric block having top, bottom, first and second end, and first and second side surfaces and having at least a second hole having a first end on the top surface, having a second end on the bottom surface, being aligned with the first hole, and being disposed between said first and second ends, said first hole spaced apart from said second hole by a predetermined distance for controlling coupling therebetween, and said first and second side surfaces, and said second hole being substantially covered with a conductive material;

a third dielectric block having top, bottom, first and second end, and first and second side surfaces and having at least a third hole having a first end on the top surface, having a second end on the bottom surface, being aligned with the second hole, and being disposed between said first and second ends, and said second end surface, said first and second side surfaces, said bottom surface, and said third hole being substantially covered with a conductive material;

means for attaching the second end surface of said first dielectric block to said first end surface of said second dielectric block and attaching the second end surface of said second dielectric block to said first end surface of said third dielectric block;

impedance means coupled to the first end of said first hole in said first dielectric block;

first coupling means coupling the transmitter signal to the second end of said second hole in said second dielectric block;

second coupling means coupled to the second end of said first hole in said first dielectric block for providing the feedback signal; and third coupling means coupling the antenna to the first end of said third hole in said third dielectric block.

* * * * *